(12) United States Patent
Basile

(10) Patent No.: US 10,155,088 B2
(45) Date of Patent: Dec. 18, 2018

(54) PREFILLED DISPOSABLE INJECTION DEVICE

(71) Applicant: Merck Sharp & Dohme Corp., Rahway, NJ (US)

(72) Inventor: Peter A. Basile, Bloomsbury, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 176 days.

(21) Appl. No.: 15/113,468

(22) PCT Filed: Feb. 27, 2015

(86) PCT No.: PCT/US2015/017900
§ 371 (c)(1),
(2) Date: Jul. 22, 2016

(87) PCT Pub. No.: WO2015/134307
PCT Pub. Date: Sep. 11, 2015

(65) Prior Publication Data
US 2017/0007766 A1    Jan. 12, 2017

Related U.S. Application Data

(60) Provisional application No. 62/090,389, filed on Dec. 11, 2014, provisional application No. 61/947,679, filed on Mar. 4, 2014.

(51) Int. Cl.
*A61M 5/24* (2006.01)
*A61M 5/31* (2006.01)
(Continued)

(52) U.S. Cl.
CPC ........ *A61M 5/2425* (2013.01); *A61M 5/3129* (2013.01); *A61M 5/31585* (2013.01); *A61M 5/5086* (2013.01); *A61M 2005/312* (2013.01)

(58) Field of Classification Search
CPC .............. A61M 5/3129; A61M 5/2425; A61M 5/3134; A61M 5/3135; A61M 5/2422;
(Continued)

(56) References Cited

U.S. PATENT DOCUMENTS 913,297 A * 2/1909 Krautschneider ... A61M 5/2425
184/38.2
2,696,212 A    9/1951 Dunmire
(Continued)

FOREIGN PATENT DOCUMENTS

EP    0400216 A1    11/1989
LV    12451B B    10/1998
(Continued)

OTHER PUBLICATIONS

International Search Report for PCT/US2015/017900 dated May 27, 2015, 9 pages.
(Continued)

*Primary Examiner* — Nathan R Price
*Assistant Examiner* — Melissa A Snyder
(74) *Attorney, Agent, or Firm* — Janet E Fair; Catherine D. Fitch

(57) ABSTRACT

A drug delivery device comprising a main body extending between distal and proximal ends comprising a hollow cylinder comprising an outer and an inner surface, wherein the inner surface comprises threads; a screw within the main body, comprising a hollow cylinder comprising an inner and an outer surface, wherein said outer surface comprises threads, wherein threads of outer surface of the screw are engaged with threads of inner surface of the main body; a plunger extending between distal and proximal ends, wherein the distal end of the plunger engages the proximal end of the screw; and a drug container extending between distal and proximal ends, and comprising a change in cross
(Continued)

section from proximal to distal end, wherein the container is within the screw, and wherein the proximal end of the drug container is fixed to the screw and distal end of the container is fixed to the main body.

11 Claims, 21 Drawing Sheets

(51) Int. Cl.
    *A61M 5/315*     (2006.01)
    *A61M 5/50*     (2006.01)

(58) Field of Classification Search
    CPC ...... A61M 2005/2433; A61M 5/31576; A61M 5/31578
    See application file for complete search history.

(56) References Cited

U.S. PATENT DOCUMENTS

| | | | |
|---|---|---|---|
| 2,911,972 A | | 9/1954 | Elinger |
| 2,888,923 A | * | 6/1959 | Da Cunha Reis ............. A61M 5/31596 604/194 |
| 3,496,937 A | * | 2/1970 | Balson .................. A61M 5/20 604/132 |
| 3,512,524 A | * | 5/1970 | Drewe .................. A61M 3/00 206/365 |
| 3,736,933 A | | 6/1973 | Szabo |
| 3,938,514 A | | 2/1976 | Boucher |
| 4,548,601 A | | 10/1985 | Lary |
| 4,810,249 A | | 3/1989 | Haber et al. |
| 5,147,311 A | * | 9/1992 | Pickhard ............... A61M 5/148 604/131 |
| 5,209,732 A | | 5/1993 | Lampropoulos et al. |
| 5,267,974 A | | 12/1993 | Lambert |
| 5,403,289 A | * | 4/1995 | Berrebi .................... A61J 1/06 604/110 |
| 5,693,021 A | | 12/1997 | Diaz et al. |
| 6,319,235 B1 | | 11/2001 | Yoshino |
| 6,916,305 B2 | | 7/2005 | Jones et al. |
| 2002/0173753 A1 | * | 11/2002 | Caizza ............... A61M 5/3234 604/241 |
| 2006/0069350 A1 | | 3/2006 | Buenger et al. |
| 2007/0051362 A1 | | 3/2007 | Sullivan et al. |
| 2007/0260188 A1 | | 11/2007 | Kelly et al. |
| 2007/0265568 A1 | * | 11/2007 | Tsals .................. A61M 5/2033 604/136 |
| 2010/0036318 A1 | | 2/2010 | Raday et al. |
| 2011/0270220 A1 | | 11/2011 | Genosar |
| 2012/0310206 A1 | * | 12/2012 | Kouyoumjian ... A61M 5/31525 604/506 |
| 2013/0281940 A1 | | 10/2013 | Gelblum et al. |

FOREIGN PATENT DOCUMENTS

| | | |
|---|---|---|
| WO | WO2003024511 A1 | 3/2003 |
| WO | WO2009146996 A1 | 12/2009 |
| WO | WO2011047298 A2 | 4/2011 |
| WO | WO2012145343 A2 | 10/2012 |
| WO | WO2013162637 A1 | 10/2013 |
| WO | WO2015134307 A1 | 9/2015 |
| WO | WO2015187518 A1 | 12/2015 |

OTHER PUBLICATIONS

International Search Report for PCT/US2015/033450 dated Aug. 31, 2015, 9 pages.
International Search Report for PCT/US2016/027019 dated Jul. 1, 2016, 9 pages.

* cited by examiner

PREFILLED DISPOSABLE INJECTION DEVICE

CROSS-REFERENCE TO RELATED APPLICATIONS

This application is a U.S. National Phase application under 35 U.S.C. § 371 of PCT Application No. PCT/US2015/017900, filed Feb. 27, 2015, which published as WO 2015/134307 A1 on Sep. 11, 2015, and claims priority under 35 U.S.C. § 365(b) from United States provisional patent application Nos. 62/090,389, filed Dec. 11, 2014, and 61/947,679, filed Mar. 4, 2014.

FIELD OF THE INVENTION

The present invention relates generally to drug delivery devices. Specifically, the invention is directed to an injection device that incorporates a collapsible drug container which cannot be refilled, preventing re-use of the drug delivery device.

BACKGROUND

A goal of many pharmaceutical companies is to make their life-saving medication available to as many people in as many countries as possible. However, in many cases cost becomes a prohibitive factor. Surprisingly, in some, if not most instances, it is not the cost of that actual medication that prohibits a treatment from becoming widely accessible but the cost of the packaging and shipping of the medication that makes it cost prohibitive. Thus, reducing the cost of packaging is one way to lower the cost of medications, enabling companies to make needed treatments more readily accessible to more patients.

The problem with traditional packaging, specifically pre-filled glass syringes, is two-fold. The first is the cost of manufacturing the glass drug container. The second is the cost of filling the glass container. Manufacturing and filling, are by their very nature are two distinct processes. The first step is to form the container. Then the glass container must be packaged and shipped to the filling facility. Once at the filling facility, the container must be unpacked and then filled.

Another issue that plagues conventional syringes is that conventional syringes can be refilled and reused. This is a major concern as reusing syringes promotes the transmission of blood borne diseases like HIV.

Thus, there is a need for a low-cost prefilled disposable syringe that cannot be refilled or reused.

SUMMARY

The present invention provides a reduced-cost injection device that incorporates a pre-filled collapsible drug container that cannot be re-filled, preventing possible re-use of the drug delivery device.

The present invention is directed to a drug delivery device comprising a main body extending between distal and proximal ends comprising a hollow cylinder comprising an outer surface and an inner surface, wherein the inner surface comprises threads; a screw situated within the main body, comprising a hollow cylinder comprising an inner surface and an outer surface, wherein said outer surface comprises threads, wherein the threads of the outer surface of the screw are engaged with the threads of the inner surface of the main body; a plunger extending between distal and proximal ends, wherein the distal end of the plunger engages the proximal end of the screw; and a drug container extending between distal and proximal ends, and comprises a change in cross section from proximal end to distal end, wherein the drug container is located within the screw, and wherein the proximal end of the drug container is fixed to the screw and the distal end of the drug container is fixed to the main body.

BRIEF DESCRIPTION OF THE FIGURES

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DESCRIPTION

Figure 1:
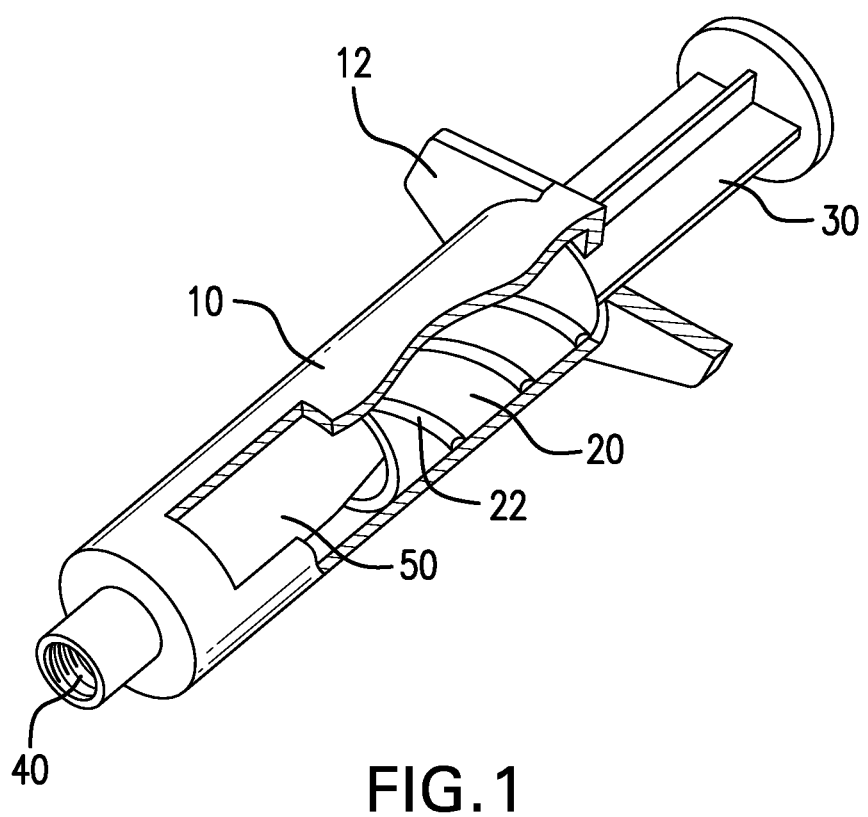
FIG. 1 is a perspective partial cutaway view of a delivery device according to an exemplary embodiment of the present invention.

The present invention is directed to a reduced-cost injection device that incorporates a pre-filled collapsible drug container that cannot be re-filled, preventing possible re-use of the drug delivery device For the purpose of clarity, orientation references are hereby established for the description of this invention. The term "proximal" refers to a position that is close to the body of the person injecting a drug into the patient with the device. The term "distal" refers to a position that is away from the body of the person injecting the drug into the patient with the device.

One of the key features of the drug delivery device described herein is that it contains a drug container that extends between distal and proximal ends. The distal end is stationary while the proximal end is capable of being twisted. As the proximal end is twisted and the distal end remains stationary, the proximal end of the tube folds on itself and constricts. Twisting initiates at the proximal end since this is the weakest cross section of the drug container. As the twisting motion continues, the constriction moves distally, emptying the contents of the drug container, delivering the drug to the patient. In certain embodiments the drug container is made of thin, flexible material, such as a thin flexible plastic. In certain embodiments, the cross-section of the drug container changes from is proximal end to its distal end. In certain embodiments, the drug container tapers from its distal end to its proximal end.

In certain embodiments, one or more inwardly projecting grooves are formed in the surface of the drug container. The groove or grooves promote thorough collapse and emptying of the drug container when it is twisted. The groove or grooves may be oriented parallel to the axis of the drug container. Alternatively, the groove or grooves may be non-parallel to the axis of the drug container. In certain embodiments, the groove or grooves are oriented diagonally across the entire length of the drug container, opposite to the direction of twisting. The groove or grooves promote complete collapse of the drug container as it is twisted, ensuring complete and consistent emptying of the drug container.

Additionally, the drug delivery device described herein includes a main body and a screw that act in concert to twist the drug container. In certain embodiments, the main body is a barrel. In certain embodiments the barrel comprises a first half and a second half, wherein the first barrel half and the second barrel half are aligned to one another by alignment means. In certain embodiments, the alignment means are projecting features on one half of the barrel, wherein the projecting features are abutted by mating features on the other half of the barrel, whereby the abutment of said features prevents relative movement between the first barrel half and the second barrel half in at least one direction. In certain embodiments, the first barrel half and said second barrel half are held together by retention means comprising any of, threaded fasteners, compression clips, solvent bonding, adhesive bonding, integral mating snap fasteners, thermal staking, thermal welding, ultrasonic welding, circumferential bands, or adhesive appliques applied to surfaces of both of said halves, or any combination of said retention means.

In certain embodiments of the drug delivery devices described herein, the screw has a first half and a second half. The first half of the screw and the second half of the screw are aligned to one another by alignment means. In certain embodiments, alignment means includes projecting features on one half of the screw, wherein the projecting features are abutted by mating features on the other half of the screw, whereby the abutment of said features prevents relative movement between the first half and the second half of said screw. In certain embodiments, the first screw half and the second screw half, once assembled and inserted into said barrel, are held together by a running clearance fit within said barrel, whereby the screw can move freely within the barrel and, whereby the screw halves cannot separate sufficiently to cause misalignment or disengagement of said screw halves.

The drug delivery devices described herein also include a plunger. In the drug delivery devices described herein, the plunger comprises a means for engaging the screw wherein the plunger and the screw are restrained from relative axial motion, and wherein the plunger and the screw can freely rotate relative to each other. In certain embodiments, the plunger has one or more circumferential projections that engage a mating circumferential groove in the inner surface of said screw. In an alternative embodiment, the screw has one or more inward-facing circumferential projections that engage a mating circumferential groove in the outer surface of said plunger. In the drug delivery devices described herein, the plunger comprises a means for preventing relative rotation of the plunger in the barrel. In certain embodiments, the plunger has a non-circular cross section for at least the length of its intended axial motion, wherein the barrel comprises a mating non-circular opening that engages the plunger, wherein the plunger is restrained from rotation relative to the barrel, wherein the plunger is fee to move axially relative to the barrel. In certain embodiments, the plunger is non-coaxial with the barrel for at least the length of its intended axial motion. In such embodiments, the barrel can comprise a mating non-coaxial opening that engages the plunger, wherein the plunger is restrained from rotation relative to the barrel and wherein the plunger is free to move axially relative to said barrel.

In a preferred embodiment, the appearance of the assembled device should be universally recognized as a syringe, such that there is no ambiguity in that the drug delivery device described herein is meant to be used like a syringe.

Embodiments of the invention are discussed in detail below. In describing embodiments, specific terminology is employed for the sake of clarity. However, the invention is not intended to be limited to the specific terminology so selected. All references cited herein are incorporated by reference as if each had been individually incorporated.

Described herein is a drug delivery device comprising a main body extending between distal and proximal ends comprising a hollow cylinder comprising an outer surface and an inner surface, wherein the inner surface comprises threads; a screw situated within the main body, comprising a hollow cylinder comprising an inner surface and an outer surface, wherein said outer surface comprises threads, wherein the threads of the outer surface of the screw are engaged with the threads of the inner surface of the main body; a plunger extending between distal and proximal ends, wherein the distal end of the plunger engages the proximal end of the screw; and a drug container extending between distal and proximal ends, and comprises a change in cross section from proximal end to distal end, wherein the drug container is located within the screw, and wherein the proximal end of the drug container is fixed to the screw and the distal end of the drug container is fixed to the main body.

In certain embodiments, the main body of the drug delivery device described herein is a barrel. In certain embodiments of the drug delivery device described herein, the inner surface of the main body comprises helical threads. In certain embodiments of the drug delivery device described herein, the outer surface of the screw has helical threads that extend along at least a portion of the outer surface of the screw. In certain embodiments of the drug delivery device described herein, the drug delivery device, further comprises a clamp, wherein the clamp is located within the screw and wherein the clamp engages the proximal end of the drug container. In certain embodiments of the drug delivery device described herein, the drug container comprises an outlet port at the distal end.

In certain embodiments the drug delivery device described herein, further comprises a needle, wherein the needle is attached to the drug container. In certain embodiments of the drug delivery device described herein, the needle is attached to the device before use.

In certain embodiments of the drug delivery device described herein, the drug container tapers from the distal end to the proximal end. In certain embodiments of the drug delivery device described herein, the drug container comprises hemispherical proximal and distal ends. In certain embodiments of the drug delivery device described herein, the drug container further comprises at least one groove. In certain embodiments of the drug delivery device described herein, the drug container is made of a flexible material. In certain embodiments of the drug delivery device described herein, the drug container further comprises a Frangible Seal at the distal end of the drug container. In certain embodiments of the drug delivery device described herein, the drug container contains a drug. In certain embodiments of the drug delivery device described herein, the drug in the drug container is oxytocin or carbetocin. In certain embodiments of the drug delivery device described herein, wherein when the drug container is twisted the drug is expelled from the drug container.

In certain embodiments of the drug delivery device described herein, the drug delivery device is manufactured using a blow-fill-seal process. In other embodiments of the drug delivery device described herein, the drug delivery device is manufactured using a form-fill-seal process.

In certain embodiments of the drug delivery device described herein, the drug delivery device, comprises a hollow cylindrical barrel extending between distal and proximal ends, comprising an inner surface and an outer surface, wherein the inner surface comprises helical threads; a screw situated within the barrel extending between distal and proximal ends, comprising a hollow cylinder comprising an inner surface and an outer surface, wherein the outer surface comprises helical threads, wherein the helical threads of the outer surface of the screw extend at least a portion of the length of the screw, wherein the helical threads of the outer surface of the screw are engaged with the helical threads on the inner surface of the barrel, wherein the engagement between the threads of the outer surface of the screw and the threads of the inner surface of the barrel is a threaded engagement, whereby the screw rotates as it translates axially along the length of said barrel; a plunger extending between distal and proximal ends, wherein the distal end of the plunger engages the proximal end of the screw, wherein axial force applied on the proximal end of the plunger in the distal direction causes the screw to translate distally within the barrel; a drug container extending between distal and proximal ends, wherein the proximal end of the drug container is fixed to the screw and the distal end of the drug container is fixed to the barrel and wherein the drug container comprises an outlet port at the distal end; and a needle attached to the distal end of the drug container, whereby motion of the plunger in the distal direction causes rotation and translation of said screw, whereby said rotation is imparted to the proximal end of the drug container, whereby said drug container is twisted, whereby the contents of the drug container are expelled through said needle.

In certain embodiments of the drug delivery devices described herein, such devices may have to be primed before use. In certain embodiments, a ratchet or linear cam mechanism can be used to permit priming without emptying the contents of the drug container in addition to preventing reinflation when the drug container is emptied.

A preferred embodiment of the invention is discussed in detail below. While specific exemplary embodiments are discussed, it should be understood that this is done for illustration purposes only. A person skilled in the relevant art will recognize that other components and configurations can be used without parting from the spirit and scope of the invention.

FIG. 1 shows one embodiment of a drug delivery device described herein. FIG. 1 is a partial cutaway view of a delivery device according to an exemplary embodiment of the present invention. The device includes a barrel 10. The barrel 10 has finger flanges 12. The device also includes a screw 20. The screw 20 is a hollow cylinder with external mating helical threads 22. As shown in FIG. 1, the external mating threads 22 span the entire length of the screw 20. In other embodiments, the external mating threads can span a portion or less than the entire length of the screw. The external mating threads 22 mate with internal threads (not shown) on the inner surface of the barrel 10.

The device also includes a plunger 30. In certain embodiments the plunger 30 engages at its distal end the proximal end of the screw. The engagement prevents relative axial motion between the plunger 30 and screw 20. The engagement permits rotational relative motion between the plunger 30 and the screw 20, whereby application of an axial force in the distal direction to the plunger 30 causes distal motion of the screw 20 and rotation of the screw 20. The combined translation and rotation of the screw 20 causes the drug container 50 to twist, thereby emptying its contents. The device also includes a needle attachment 40 so that a needle can be attached to the drug delivery device. As shown in FIG. 1 the needle attachment is a threaded attachment (needle not shown). However, in certain embodiments, the mechanical engagement of the needle to the drug delivery device comprises any of, a Luer Lock, Luer taper, tapered connection, helical threads, a bayonet fitting connection, or an integral latch feature. In certain embodiments, the needle is attached to the drug delivery device prior to use. In certain embodiments, the needle is directly attached to the drug container.

Figure 2:
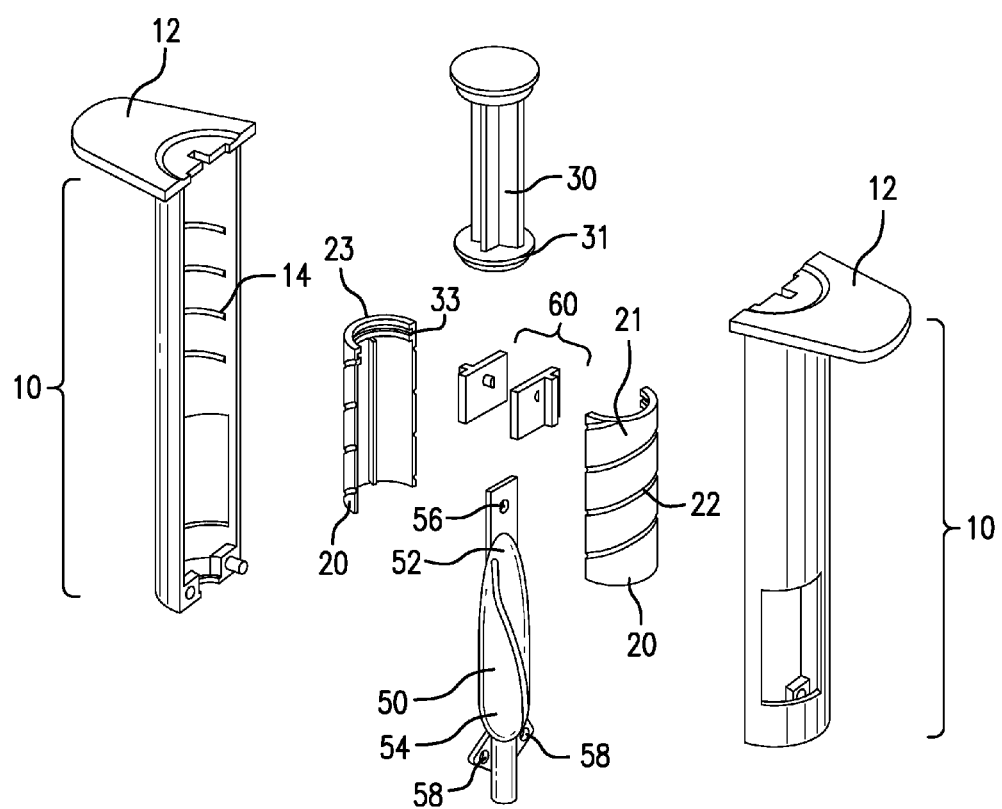
FIG. 2 is an exploded view of the device of according to an exemplary embodiment of the present invention.

FIG. 2 is an exploded view of the drug delivery device of according to an exemplary embodiment of the present invention. The device includes a barrel 10. The barrel 10 has finger flanges 12. The barrel 10 has internal high lead helical threads 14 on its inner surface. The device also includes a screw 20. The screw 20 is a hollow cylinder comprising two halves, a first half 21 and a second half 23, wherein each half comprises an outer surface with external mating helical threads 22 that mate with the internal high lead helical threads 14 in the barrel 10. As shown in FIG. 2 the external mating threads 22 span the entire length of the screw 20. In other embodiments, the external mating threads can span less than the entire length of the screw.

The drug delivery device of FIG. 2 also includes a plunger 30. As shown in FIG. 2 the distal end of the plunger 30 engages the screw at the proximal end of the screw. In FIG. 2 the plunger 30 has a circumferential projection 31 that engages a circumferential groove 33 on the screw. The engagement prevents relative motion in an axial direction between the plunger 30 and the screw 20, but permits rotational motion between the plunger 30 and screw 20. Application of axial force in the distal direction to the proximal end of the plunger causes axial movement of the plunger 30 in the distal direction of plunger 30. This motion is transferred to screw 20 by means of the engagement between the plunger 30 and the screw 20. The threaded engagement between the external threads 22 of screw 20 and the internal threads 14 of barrel 10 causes the screw 20 to rotate as it moves in an axial direction within the barrel 10.

The device also comprises a drug container 50. The drug container 50 tapers from its distal end 54 to its proximal end 52. The drug delivery device also includes a clamp 60 that secures the drug container 50 to the screw 20. The drug container 50 comprises a securing mechanism at its proximal end 52, wherein the drug container 50 is secured to the clamp 60 at the proximal end 52 of the drug container 50.

In FIG. 2 the securing mechanism is a hole 56 at the proximal end 52 of the drug container 50. In this embodiment the drug container 50 also has a securing mechanism at its distal end 54, wherein the drug container 50 is secured to the barrel 10 at the distal end 54 of the drug container 50. The securing mechanism is a set of two holes 58 located at the distal end 54.

Figure 3:
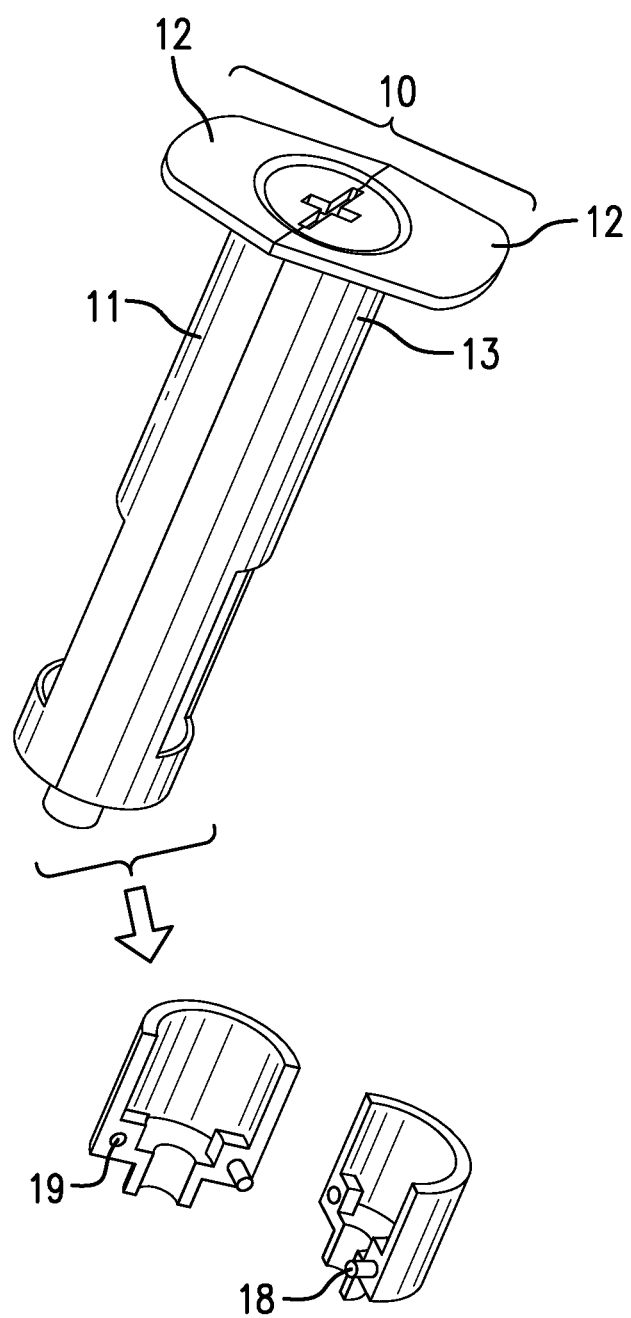
FIG. 3 is a perspective view of a barrel according to an exemplary embodiment of the present invention and a detailed view of alignment features for locating and aligning the first half and second half of the barrel.

FIG. 3 is a perspective view of the barrel 10 according to an exemplary embodiment of the present invention and a detailed view of alignment features for locating and aligning the first half and second half of the barrel. The device includes a barrel 10. The barrel 10 has finger flanges 12. As shown in FIG. 3, the barrel 10 comprises a first half 11 and a second half 13. However in other embodiments the barrel may comprise a single component. In the embodiment of FIG. 3 the barrel 10 comprises a first half 11 and a second half 13, wherein the two halves engage one another, wherein the engagement comprises locating pins 18 and holes 19. In alternate embodiments, other means of locating the two components may be used, comprising tabs and slots, stepped surfaces, ribs, or any combination thereof. In an exemplary embodiment of the invention, the first half 11 and second half 13 are identical to one another. In an alternate embodiment, the first half 11 and second half 13 of the barrel are not identical to one another.

Figure 4:
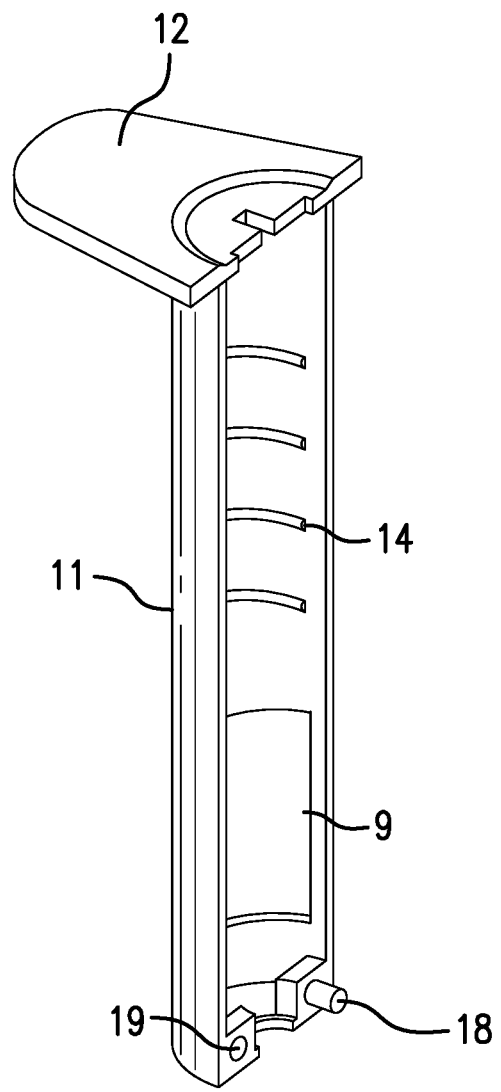
FIG. 4 is a detailed view of one half of a barrel according to an exemplary embodiment of the present invention.

FIG. 4 is a perspective view of the first half 11 of the barrel with flange 12. In the exemplary embodiment shown in FIG. 4, the inner surface of the barrel comprises high lead threads 14. The barrel also comprises a view port 9. In the exemplary embodiment shown in FIG. 4, one or more locating pins 18 engage with one or more locating holes 19 to align and engage the first half 11 of the barrel with the second half. In another embodiment, each barrel half can comprise both locating pins and holes. In another embodiment, the first half 11 of the barrel is identical to the second half. In an alternate embodiment, the first half is not identical to the second half.

Figure 5:
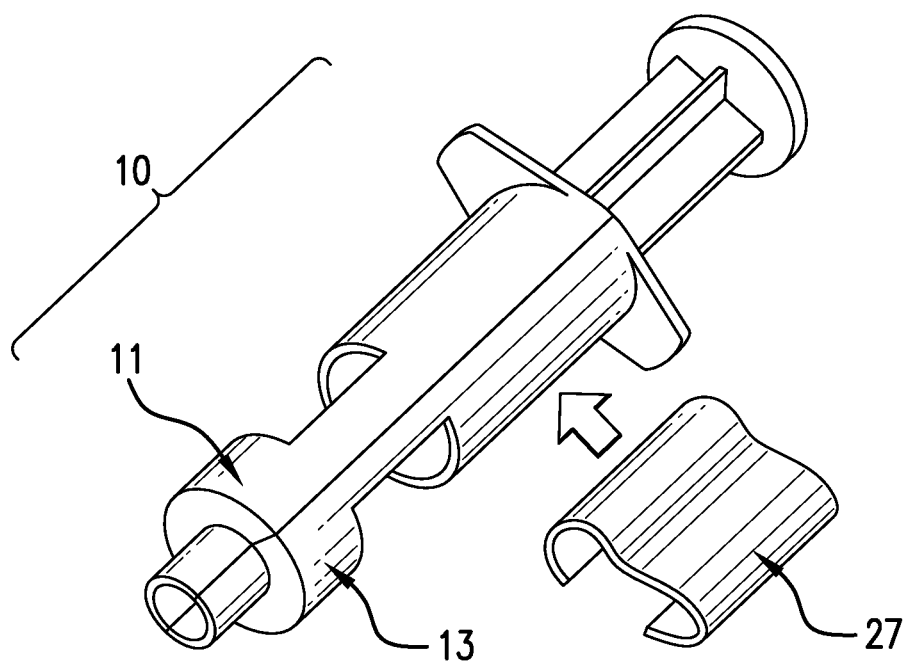
FIG. 5 is a perspective view of an adhesive label that is applied to both the first half and the second half of a barrel, according to an exemplary embodiment of the present invention.

FIG. 5 is a perspective view of an embodiment of a barrel 10, wherein, the first half 11 and second half 13 of the barrel are held together by an adhesive applique 27 that spans the interface between both halves of barrel 10 and adhesively attaches to the surface of the barrel 10. In an alternate embodiment, the adhesive applique 27 also functions as an identifying label.

Figure 6:
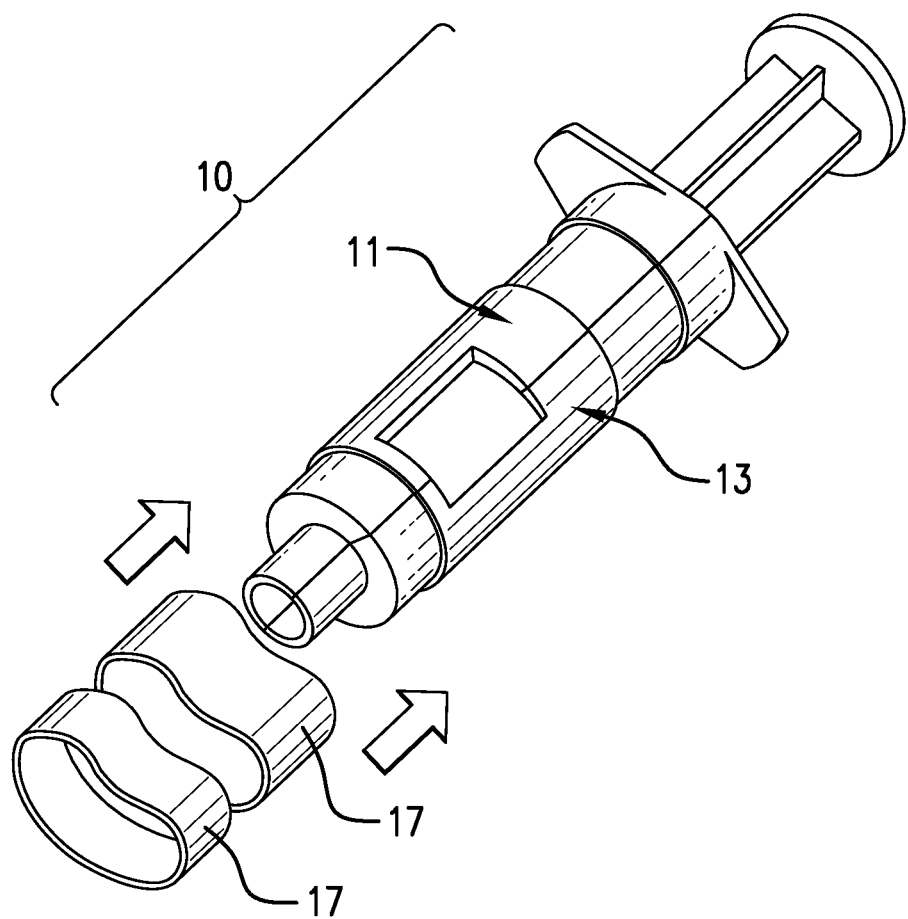
FIG. 6 is a perspective view showing circumferential bands that can be applied over a barrel, according to an exemplary embodiment of the present invention.

FIG. 6 is a perspective view of an exemplary embodiment of the present invention, wherein the first half 11 and second half 13 of the barrel 10 are held together by one or more circumferential bands 17 which are applied to the barrel 10. In one embodiment, such circumferential bands may have elastic properties to provide tensile force required to hold the first half and second half together, and are stretched, positioned into place, and released once in position. In an alternate embodiment, tensile bands may comprise a single wide filament of material that is stretched while wrapped at least once around the barrel. Securing the free-end of the filament after wrapping can be achieved by adhesive means or localized thermal bonding means. In an alternate embodiment, the bands 17 may comprise heat-shrink film that is heated locally after positioning in place to locate the first barrel half 11 in engagement with the second barrel half 13.

Figure 7:
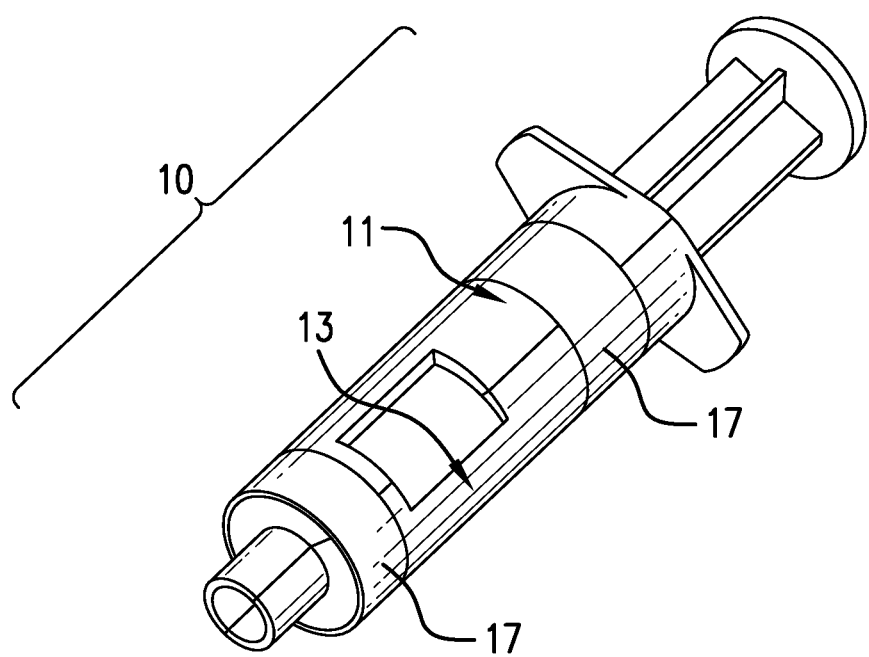
FIG. 7 is a perspective view of retaining bands in place around a barrel, according to an exemplary embodiment of the present invention.

FIG. 7 is a perspective view showing the circumferential bands 17 in place on the barrel 10, holding the first half 11 and the second half 13 of the barrel 10 together. In an alternate embodiment, the circumferential bands 17 also function as an identifying label.

Figure 8:
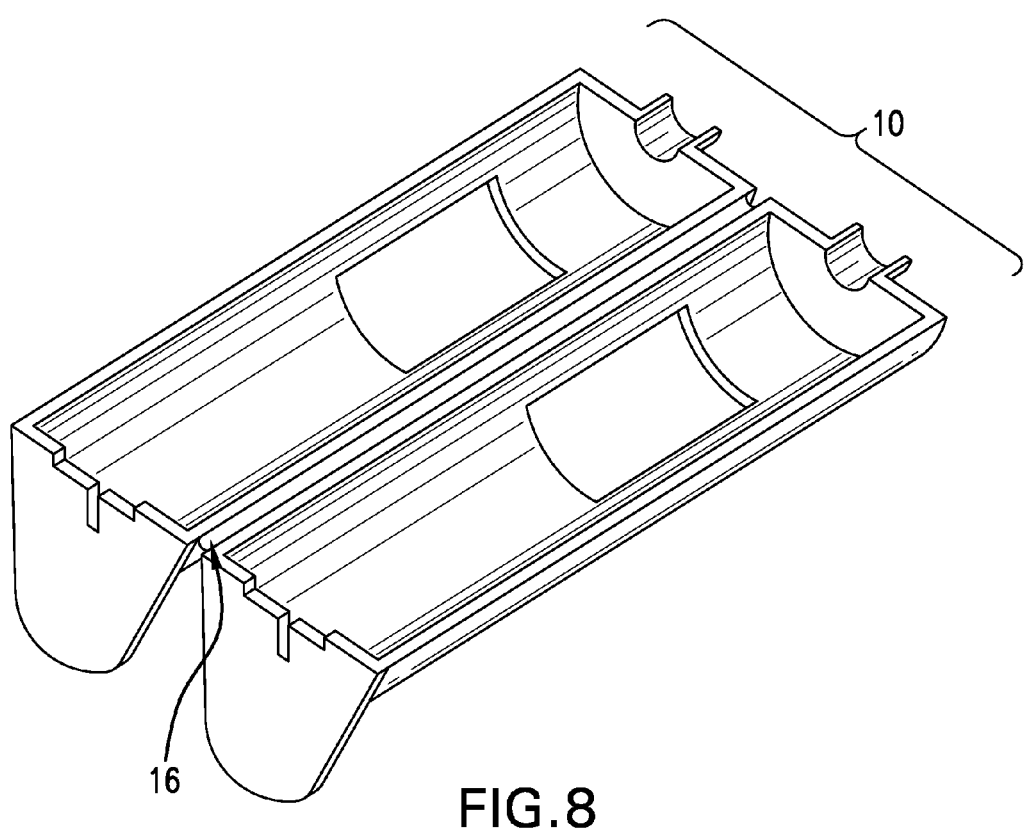
FIG. 8 is a perspective view of a barrel, with hinge feature connecting the first half and the second half of the barrel, according to an exemplary embodiment of the present invention.

FIG. 8 is a perspective view of an alternate embodiment of a barrel of the drug delivery devices described herein. The barrel 10 is a molded single part, wherein the part comprises the first half and second half connected by a thin integral hinge 16. The hinge permits assembly of all of the above-mentioned internal components of the invention into the first of barrel 10, whereby the second half may then be closed by means of the hinge 16.

Figure 9:
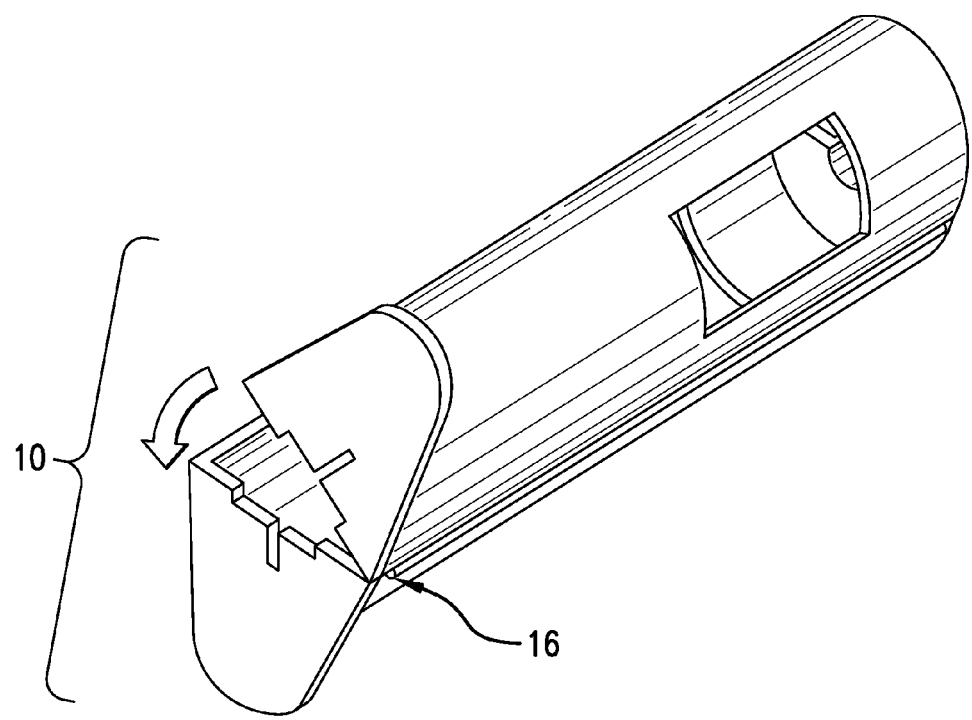
FIG. 9 is a detailed view of the hinge feature connecting the first half and second half of a barrel, according to an exemplary embodiment of the present invention.

FIG. 9 is a detailed view of a portion of the barrel 10 of FIG. 8, as barrel 10 is being closed, showing hinge 16.

Figure 10:
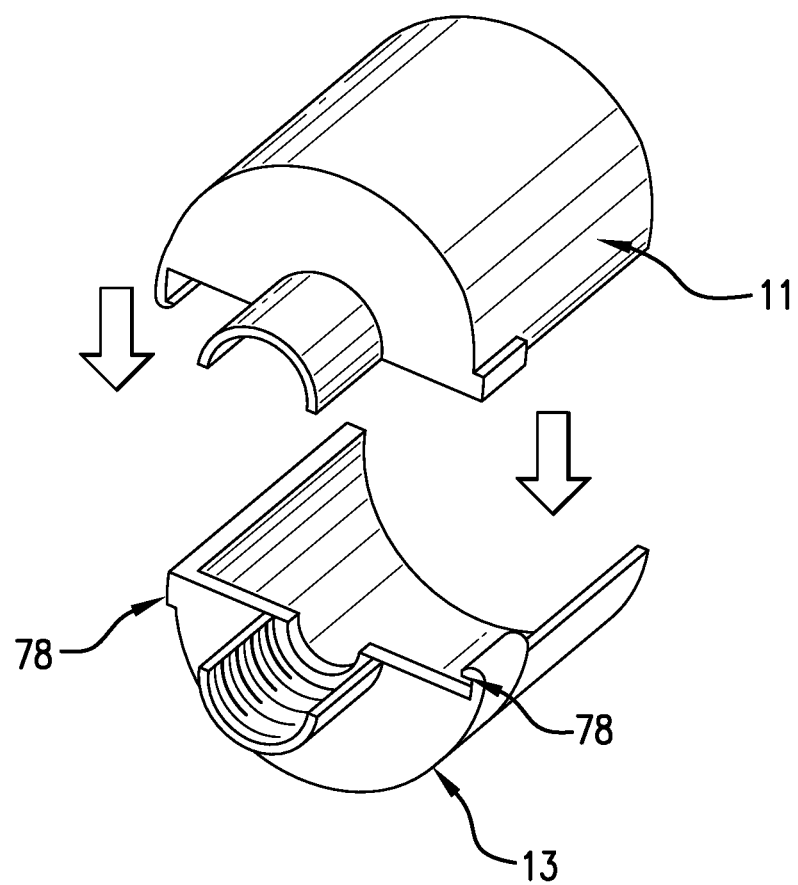
FIG. 10 is a detailed view of latch features in a barrel, according to an exemplary embodiment of the present invention.

FIG. 10 is a detailed view of a latch feature in a barrel, according to another embodiment of the drug delivery devices described herein. FIRGURE 10 shows latching geometry 78, which creates a snap fit that holds the first half 11 and second half 13 of the barrel together. In certain embodiments, the latching geometry is also capable of engaging and retaining the drug container at its distal end.

Figure 11:
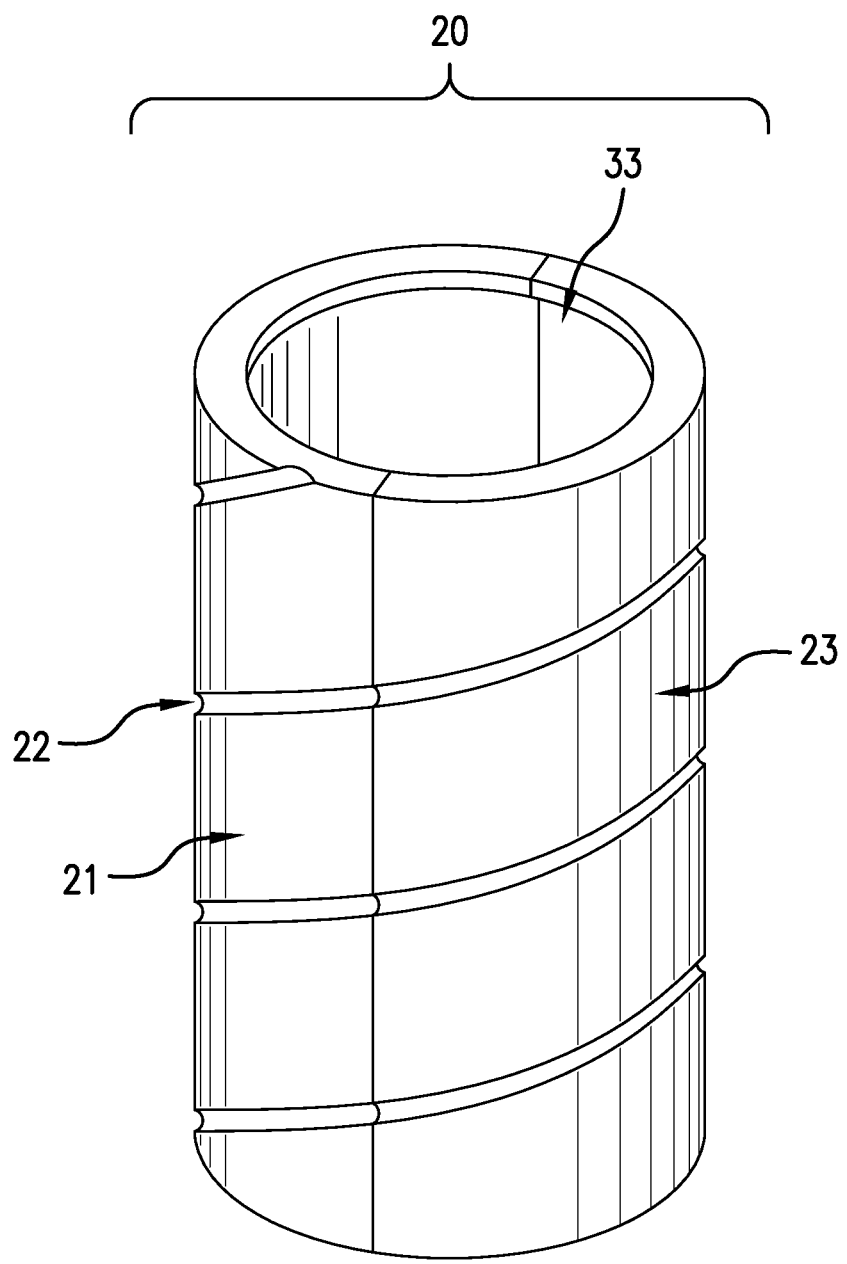
FIG. 11 is a perspective view of a screw, according to an exemplary embodiment of the present invention.

FIG. 11 is a perspective view of the screw 20 according to an exemplary embodiment of the present invention. The screw comprises external threads 22 which engage mating threads on the inner surface of the barrel. As shown in FIG. 11, the screw 20 comprises a first half 21 and a second half 23. In an alternate embodiment, the screw can comprise a single part.

Figure 12:
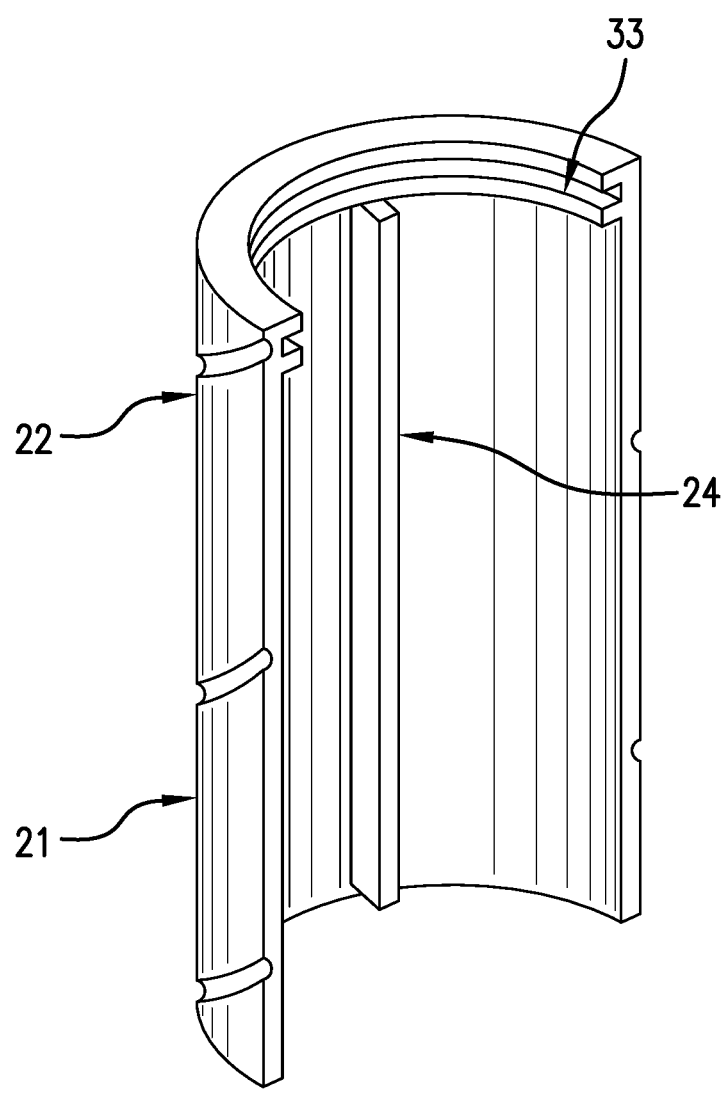
FIG. 12 is a detailed view of one half of a screw, according to an exemplary embodiment of the present invention.

FIG. 12 is a perspective view of the first half 21 of the screw 20. As shown in FIG. 12, the internal surface of the first half 21 of the screw comprises an inwardly protruding rail 24 for engaging the clamp. Additionally, the first half 21 of the screw 20 comprises a circumferential groove 33 for engaging the plunger. In certain embodiments, the first half of the screw is identical to the second half of the screw. In an alternate embodiment, the first half of the screw and the second half of the screw are not identical, but share complimentary geometry that comprises, at a minimum, the rail, and the external thread.

The rail allows a clamp to slidingly engage the screw whereby the clamp can slide within the screw along the length of the screw, but it cannot rotate significantly relative to the screw. In certain embodiments, the screw has two rails that are oriented parallel to the axis of the screw. In another embodiment, the rails may be generally axially oriented but with a helical twist. In yet another embodiment, the screw comprises two diametrically-opposed rails. In alternative embodiments the screw may comprise a single rail, or multiple rails, where the angular spacing between rails remains constant along their length. In still another embodiment of the present invention, the first half and the second half of the screw are held together by a running clearance fit within the barrel. In other embodiment the first half and the second half of the screw are held together by snap fits, ultrasonic welding, solvent bonding, or any suitable method typically used in the permanent assembly of such components.

Figure 13:
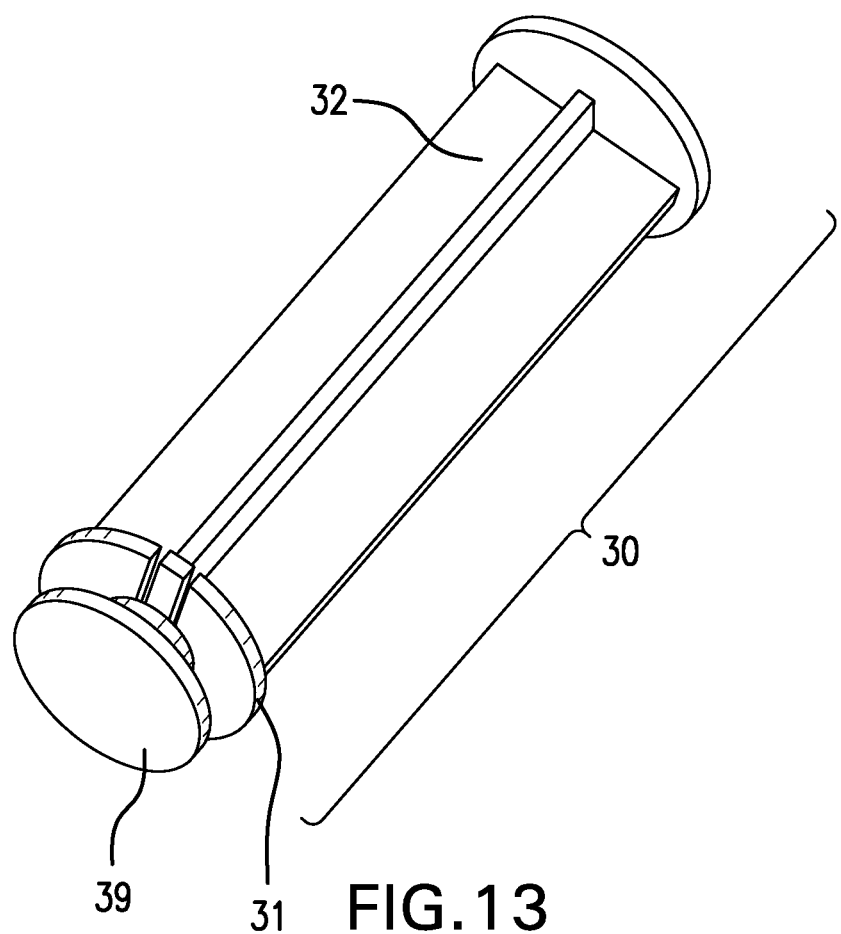
FIG. 13 is a perspective view of a plunger, according to an exemplary embodiment of the present invention.

FIG. 13 is a detailed view of plunger 30 according to an exemplary embodiment of the present invention. As shown in FIG. 13, the plunger 30 has a shaft 32 with a cruciform cross section. This cross section slides within a similarly shaped opening in the barrel to prevent rotation of the plunger 30 within the barrel. It can be readily envisaged that any non-circular cross section would prevent relative rotation between the plunger and barrel. In an alternative embodiment, a shaft with a circular or non-circular cross section positioned non-coaxially with the barrel would prevent rotation of the plunger within the barrel. The distal end 39 of the plunger 30 is shaped to engage the proximal end of the screw, wherein the plunger and screw cannot be separated axially, wherein the screw is free to rotate relative to the plunger 30. As shown in FIG. 13, the distal end 39 of the plunger 30 comprises a circumferential groove 31 that engages a mating inwardly extending circumferential rib on the inner surface of the screw. In alternate embodiments, other means of connecting the plunger and the screw may be used that would prevent relative axial movement while allowing relative rotation. These include but are not limited to one or more outwardly extending circumferential rib on the plunger engaging a circumferential groove on the inner surface of the screw.

Figure 14:
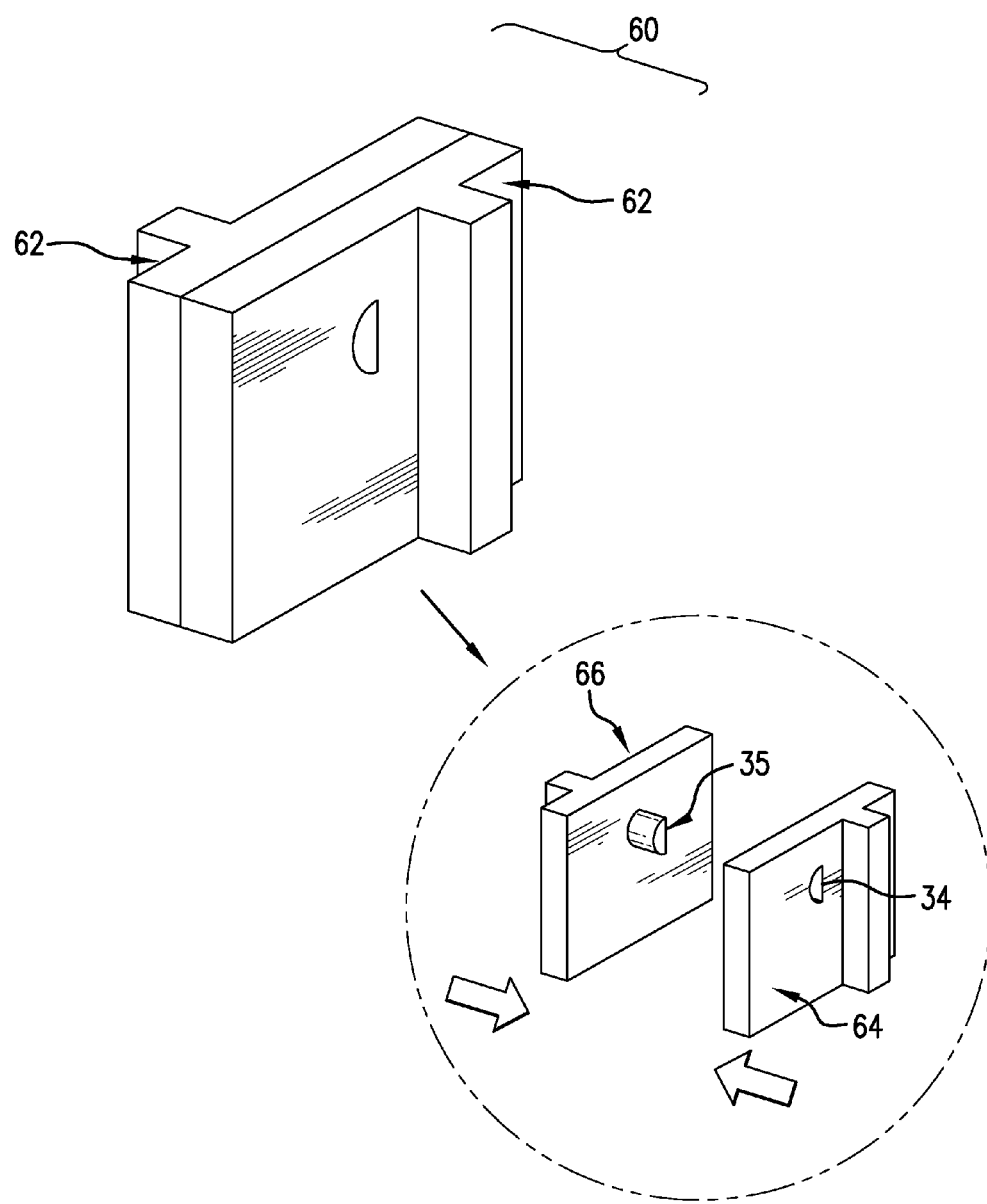
FIG. 14 is a perspective view of a clamp, according to an exemplary embodiment of the present invention and a detailed view of the first clamp half and the second clamp half, according to an exemplary embodiment of the present invention.

FIG. 14 is a perspective view of clamp 60 according to an exemplary embodiment of the present invention. In the embodiment shown in FIG. 14, clamp 60 comprises corner features 62, a first half 64 and a second half 66. The second half 66 comprises a pin 35 that engages a hole 34 in the first half 64. The pin can also engage a hole on the proximal end of drug container to ensure engagement with the clamp. In an alternative embodiment, both the first half and the second half comprise a portion of the pin, whereby when the first half and the second half are engaged, the pin portions mate along adjacent surfaces to form a complete pin. The first half and second half of the clamp may be held in engagement using latching geometry, adhesives, solvent bonding, or thermal welding.

Figure 15:
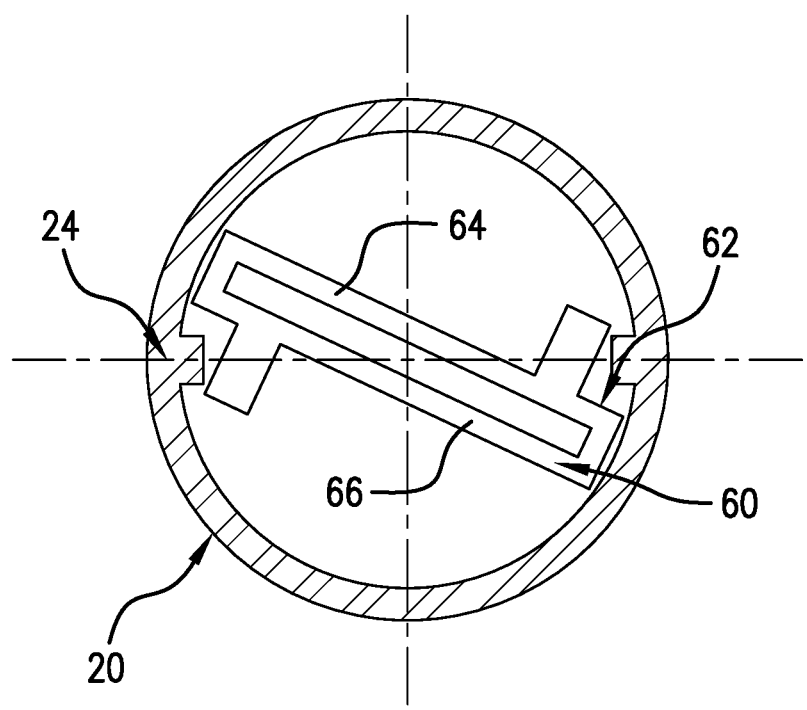
FIG. 15 is a detailed view of a clamp positioned inside a screw, according to an exemplary embodiment of the present invention.

FIG. 15 is a detailed view of a preferred embodiment of clamp 60, wherein the clamp 60 is engaged within the screw 20. The corner features 62 of the clamp 60 forms recesses that engage the ribs 24 of the screw 20, to prevent rotation of the clamp 60 within the screw 20. In an exemplary embodiment of the present invention, the first half 64 and second half 66 of the clamp 60 are held in engagement by a close running fit inside the screw 20. In an exemplary embodiment, the first half 64 and second half 66 of the clamp each comprise a corner 62, wherein each corner entraps a rail 24 of the screw, whereby the clamp 60 may slide longitudinally along the length of screw 20, and whereby the clamp 60 cannot rotate relative to the screw 20. Prevention of relative rotation between clamp 60 and screw 20 permits clamp 60 to transmit torque from the screw 20 to the drug container. In an alternative embodiment, the clamp may comprise slots that engage the rails to prevent rotation between the clamp and screw.

Figure 16:
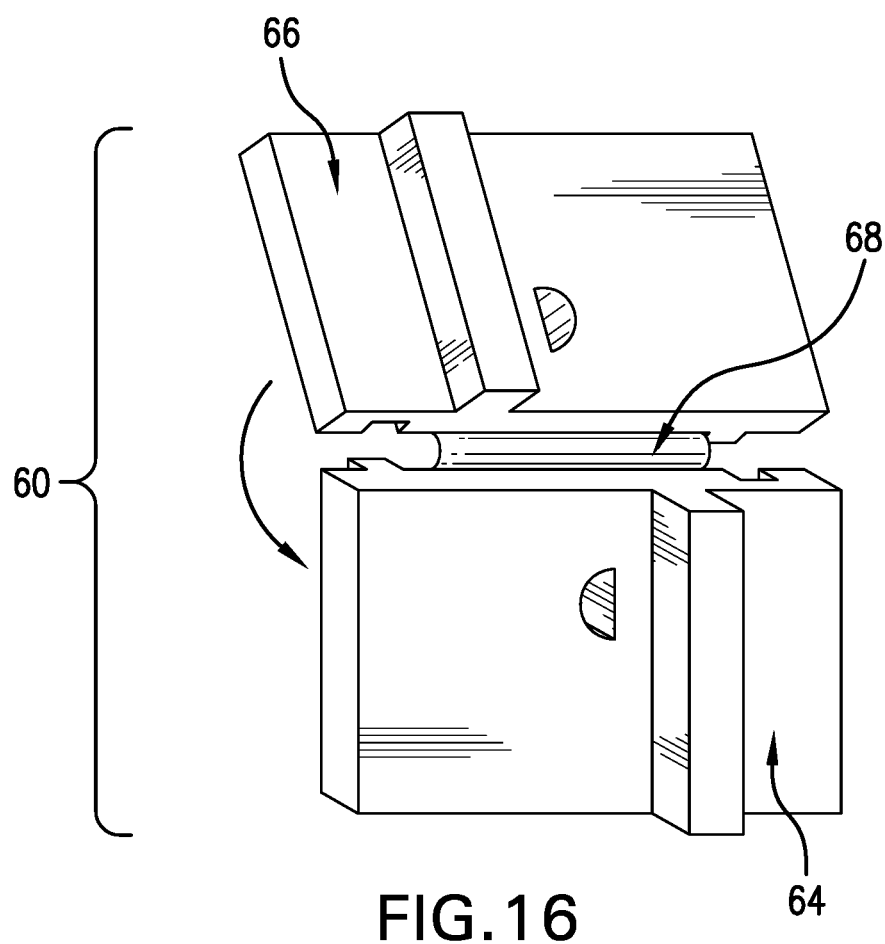
FIG. 16 is a perspective view of a clamp, showing the first clamp half and the second half of the clamp connected by a hinge feature, according to an exemplary embodiment of the present invention.

FIG. 16 is a perspective view of an embodiment of clamp 60, wherein the first half 64 and the second half 66 are held together by an integrally molded hinge 68. The hinge 68 allows the clamp 60 to open and receive the proximal end of the drug container, then close to engage the drug container. The hinge 68 also allows the clamp 60 to be molded as a single part.

Figure 17:
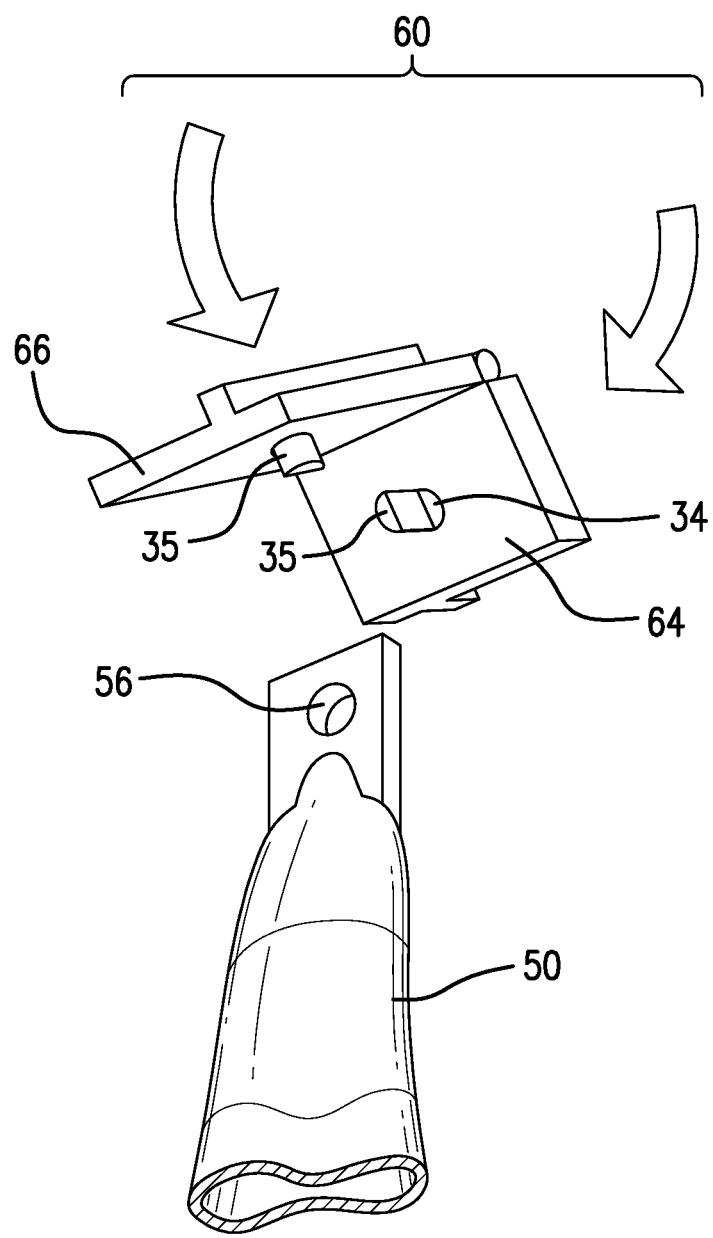
FIG. 17 is a perspective view of a clamp, according to an exemplary embodiment of the present invention showing how it engages the drug container.

FIG. 17 is a perspective view of an embodiment of clamp 60, wherein the first half 64 and the second half 66 are folded into engagement by means of hinge 68. The drug container 50 is engaged by means of pin 35 which is inserted into the hole 56 of drug container 50 when the clamp 60 is closed over drug container 50.

In certain embodiments and as shown in the figures, the clamp engages the proximal end of the drug container, such that the clamp is retained within the screw and wherein the clamp engages the screw, such that the clamp and the screw cannot rotate freely relative to each other such that the clamp is free to move axially within said screw. To accomplish this, in certain embodiments of the drug delivery devices described herein, the inner surface of the screw comprises one or more rails oriented generally parallel to the axis of said screw, wherein the angular spacing between rails is constant along the length of said rails and wherein the clamp comprises mating recesses to receive said rails.

In other embodiments, the inner surface of the screw comprises one or more grooves oriented generally parallel to the axis of the screw, wherein the circumferential spacing between multiple grooves is constant along the length of said grooves, and wherein the clamp comprises mating projections which are received by said grooves.

In certain embodiments, the clamp comprises one or more parts, wherein the drug container is secured between opposing surfaces of the clamp, wherein said opposing surfaces of the clamp are held in proximity to one another by a running clearance fit of the clamp within the screw, whereby the clamp halves cannot separate sufficiently to cause misalignment or disengagement of said clamp halves. In other embodiments, wherein the clamp comprises one or more parts, the drug container is secured between opposing surfaces of the clamp, and the opposing surfaces of said the clamp are held in proximity to one another by one or more means comprising: integral latching features in said clamp, matching projecting features and receptacles in said mating surfaces, swaging of projecting features, thermal welding, solvent bonding, and adhesive bonding.

In certain embodiments, wherein said clamp comprises a single part, mating features of the clamp can be connected by one or more integral hinges, wherein the integral hinges permit the mating features to be positioned to secure the drug container.

Figure 18:
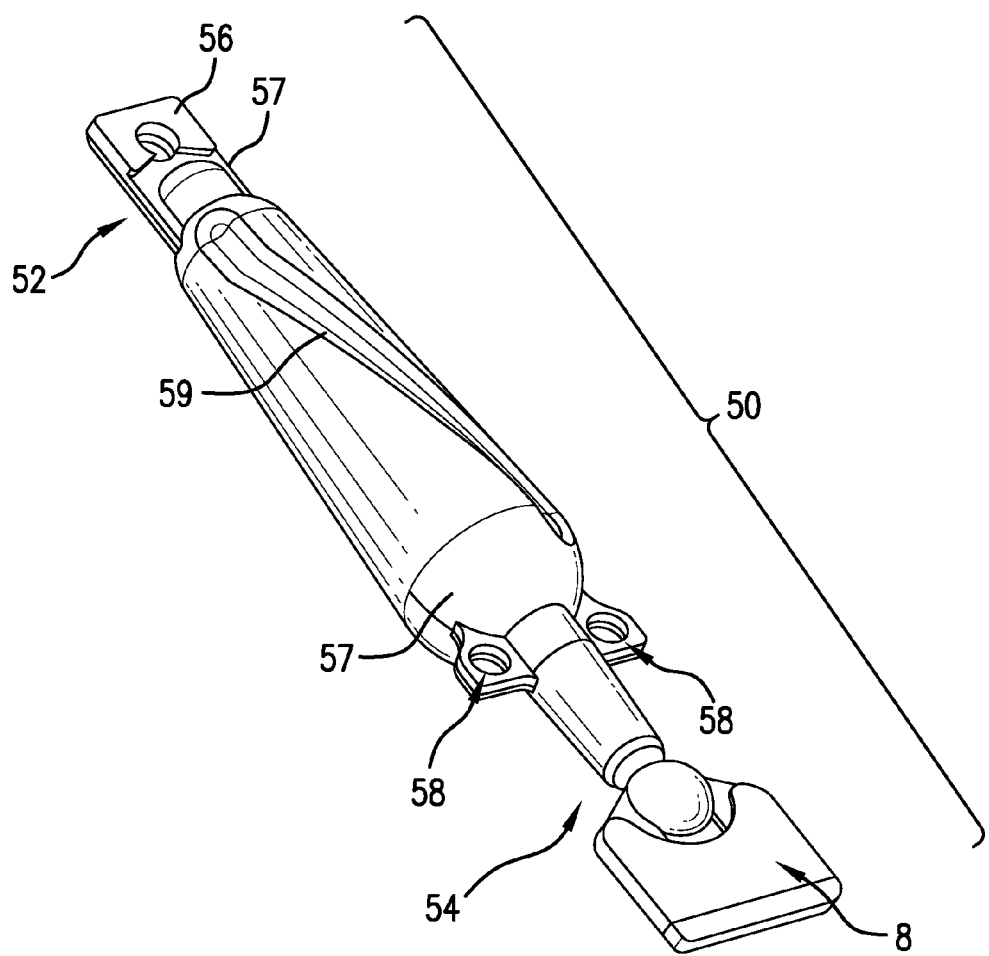
FIG. 18 is a perspective view of a drug container in its position prior to use according to an exemplary embodiment of the present invention.

FIG. 18 is a detailed view of a drug container 50 in its position prior to use according to an embodiment of the present invention. The drug container has means for securing both proximal and distal ends of the drug container to mating portions of the drug delivery device. In certain embodiments, the means for securing both proximal and distal ends of the drug container to mating portions of the drug delivery device are found in the non-drug carrying areas of the drug container. As shown in FIG. 18, drug container 50 contains a hole 56 at the proximal end 52 of the drug container. The hole 56 engages with a pin and hole lock system of the clamp in order to secure drug container 50 to the clamp. The drug container 50 also comprises holes 58 on the distal end 54 of the drug container to engage the barrel of the drug delivery device so that as the drug delivery device is being used and torque is transferred from the screw to the proximal end 52 of the drug container, the distal end 54 of drug container 50 is held stationary, allowing the drug container to twist and discharge its contents. It should be clear to anyone skilled in the art that other means of securing the proximal end of the drug container to the clamp, and securing the distal end of the drug container to the barrel may also be used. Such alternative embodiments include any of entrapping a projection from the drug container in a mating recess in the clamp or barrel, adhesive bonding, solvent bonding, thermal swaging, thermal welding, or ultrasonic welding, or any combination of the above.

In certain embodiments, the means of securing both proximal end 52 and distal end 54 of the drug container 50 to mating portions of the drug delivery device can be projections or openings produced in the non-drug carrying areas of the drug container. Such securing means are enabled by engaging the securing features in the drug container with matching receptacles or projections in the drug delivery device. In alternate embodiments, projecting features can be swaged or thermally welded to create a secure attachment between the drug container and the drug delivery device. Alternatively, the securing means on the non-drug carrying areas of the drug container 50 can be solvent bonded or adhesively bonded to mating parts of the drug delivery device.

As shown in FIG. 18, the drug container 50 tapers from its distal end 54 to its proximal end 52. Tapering of the drug container enables it to collapse in a more controlled and more complete way when it is twisted, starting from the end with the smallest cross section and propagating along its length to the end with the largest cross section. In an alternate embodiment, the proximal and distal ends of the drug container 50 comprise hemispherical shapes 57, which promote controlled and complete collapse and evacuation of the drug container when it is twisted. In certain embodiments, the drug container comprises a groove or narrow trough 59 extending at least partially along its length. The groove 59 enables more complete and more consistent collapse of drug container 50 as it is twisted, promoting more complete and more consistent emptying of drug container 50. In certain embodiments, as shown in FIG. 18, the groove 59 is non-parallel to the axis of the drug container, and is oriented in the direction of twist of the drug container 50. In an alternate embodiment of the invention, the groove may be parallel to the axis of the drug container. In other embodiments there are two grooves, diametrically opposed and oriented in the same direction with respect to twisting of the drug container.

The drug containers described herein include an outlet port. In certain embodiments, the outlet port has a Luer taper for connecting a needle to the drug container. In certain embodiments, drug container 50 is manufactured with an integrally molded, twist-off tab 8 at its distal end 52.

When tab 8 is removed the needle hub has access to the appropriately geometry, wherein the needle can be attached to such geometry. In another embodiment, a film or foil seal can be removed from the opening on the drug container's proximal end. In another embodiment, the distal end of the drug container can be pierced by an extension of the needle in the proximal direction, so that the needle pierces the distal end of the drug container when it is secured to the device. In another embodiment, the distal end of the drug container is manually pierced or cut off by the user prior to use. In certain alternate embodiments, the drug delivery device described herein further comprises a needle in communication with the outlet port of the drug container.

The drug container may be produced using a variety of manufacturing methods. In a preferred embodiment, the blow-fill-seal technique would be used. In certain embodiments, the drug container is made of thin flexible plastic. Many materials may be used in the manufacture of the drug container, but in a preferred embodiment polypropylene or polyethylene would be used. Additives to improve mechanical or processing properties may also be used, such as vinyl acetate, or metallocene. In an alternate embodiment, a thermoplastic elastomer maybe used. In an alternate embodiment, a multi-layer barrier film may be used, depending on drug container performance requirements. It should be obvious to those skilled in the art that most of these alternate embodiments may be combined to create a drug container with desired attributes suitable for specific applications.

Figure 19:
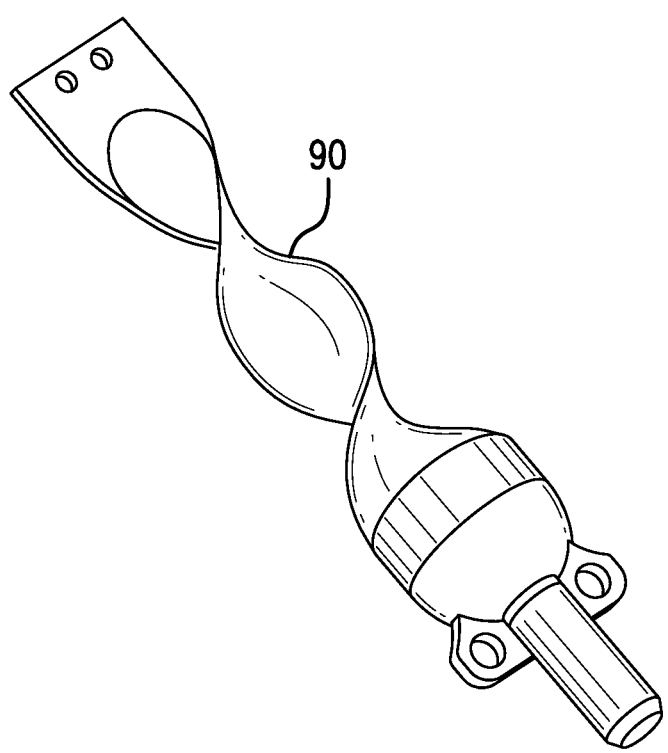
FIG. 19 illustrates a drug container in its position post use according to an exemplary embodiment of the present invention.

FIG. 19 illustrates a drug container in its position post use according to an exemplary embodiment of the present invention. The collapsed drug container 90 cannot be refilled, because the materials comprising the drug container are sufficiently flexible and non-elastic so as to significantly reduce the tendency of the drug container to return to its initial shape and volume, whereby untwisting the drug container does not create the vacuum required to re-introduce fluid into it. In addition, the helix angle of the mating threads on the screw and barrel, combined with the coefficient of friction between the barrel and screw can be chosen to prevent movement of the screw in the barrel if an untwisting torque is exerted by the drug container, whereby torque exerted directly on the screw would not result in movement of the screw.

In contrast, when the plunger of a used standard syringe is pulled back after use, a vacuum is created and the syringe can be refilled and reused which could lead to cross contamination of viruses and other diseases such as HIV.

Figure 20:
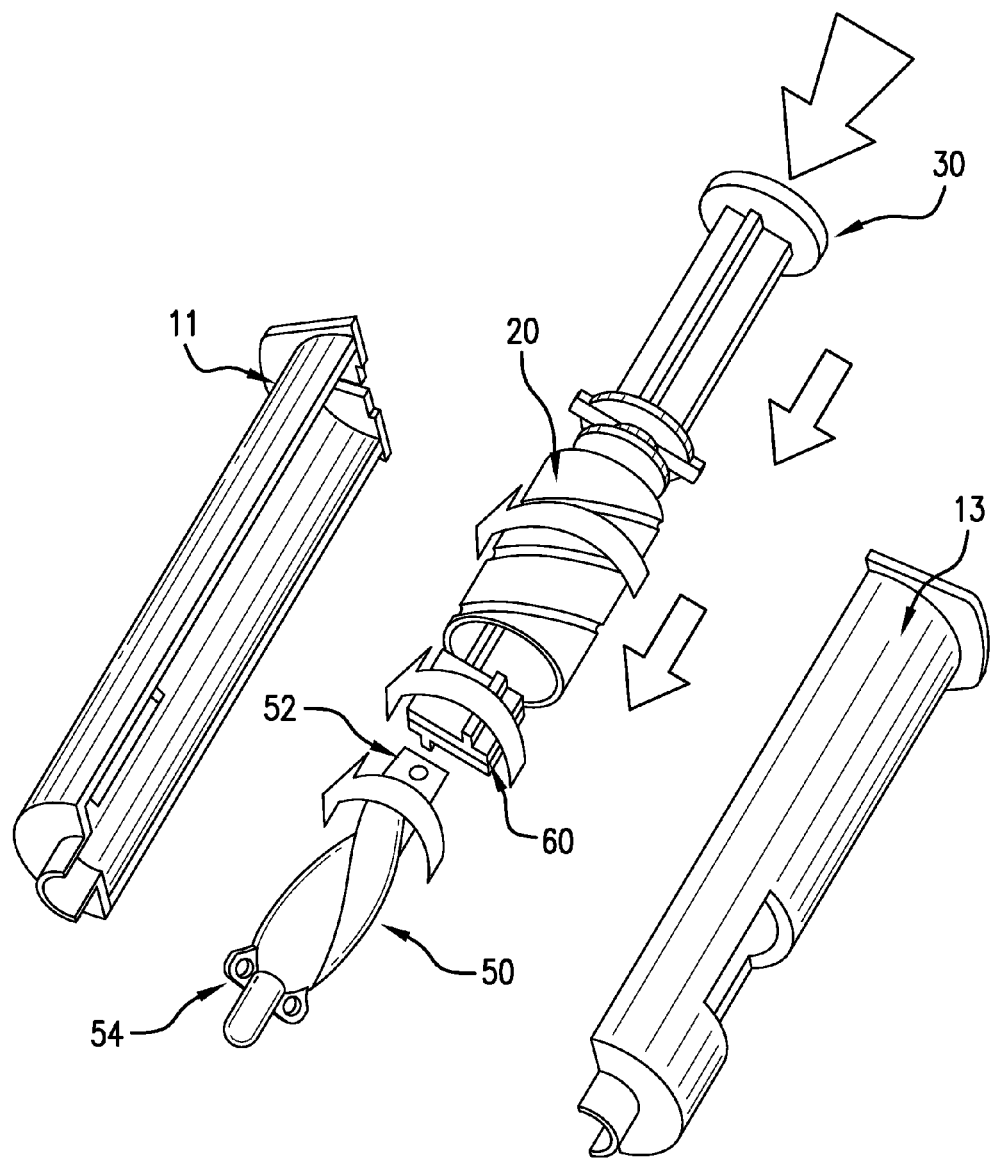
FIG. 20 is an exploded view of the device showing the motions of a plunger, a screw, the clamp, and a drug container during dispensing of the drug.

FIG. 20 is an exploded view showing the motions of all of the moving components of an embodiment of a drug delivery device described herein. Axial force applied to plunger 30 causes axial movement of the plunger 30 in the distal direction. Axial movement of plunger 30 causes a corresponding axial movement of the screw 20 in the distal direction. Axial movement of the screw 20 also causes the screw 20 to rotate by means of the threaded engagement of the screw 20 to the barrel 10. The barrel 10 comprises a first half 11 and a second half 13. Rotational movement of the screw 20 causes a corresponding rotational movement of the clamp 60. The engagement of the clamp 60 to the proximal end 52 of the drug container 50 creates a rotational movement of the proximal end of the drug container 50. The distal end 54 of the drug container 50 is fixed to the barrel 10 and is stationary. The resultant twisting motion of drug container 50 causes it to expel its contents.

Figure 21:
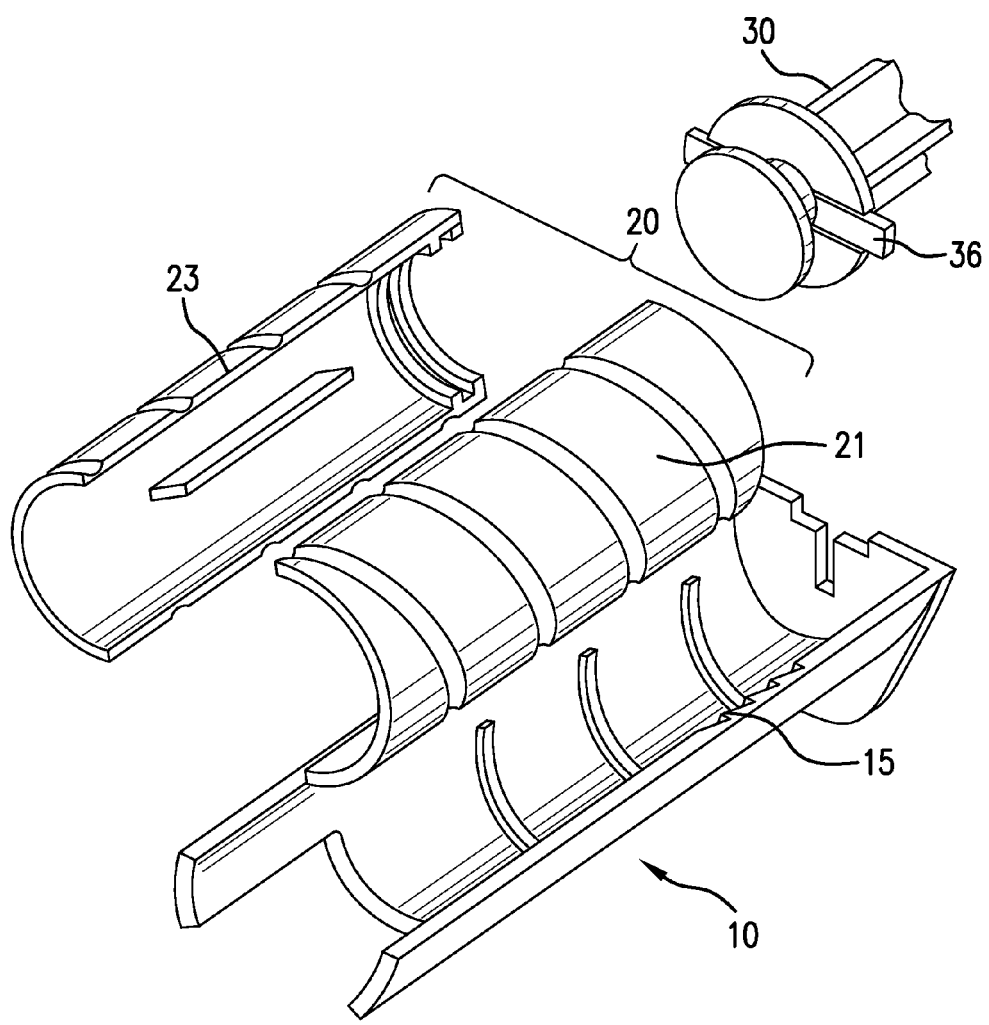
FIG. 21 is a perspective view of an optional non-return feature added to the interface of the plunger and the barrel.

FIG. 21 is a perspective view of an optional non-return feature added to the interface of the plunger and the barrel. Such a feature is intended to be a backup to the non-reinflating characteristic of the drug container, to further ensure that the plunger can only move in the distal direction. FIG. 21, shows screw 20 comprising a first half 21 and a second half 23, barrel 10 and the distal portion of plunger 30. As shown in FIG. 21, diametrically opposed radially-extending tabs 36 located at the distal end of the plunger 30 interact with a series of teeth 15 built into either side of the barrel 10 to prevent the plunger from ever being retracted.

The drug delivery device can be used to deliver any type of drug that can be delivered via a syringe. In some embodiments of the drug delivery device described herein, the drug container contains oxytocin or carbetocin. In certain embodiments the drug delivery device described herein, the drug container is pre-filled with a drug such as oxytocin or carbetocin.

The various components of the drug delivery devices described herein are preferably made of a biocompatible, non-biodegradable polymer. Suitable biocompatible, non-biodegradable polymer include but are not limited to, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; a polyethylene; a polypropylene; a metallocene plastomer, a thermoplastic elastomer, an acrylic, a polycarbonate, an acrylonitrile-butadiene-styrene, a multi-layer barrier film; or a blend, combination, or copolymer thereof. Each component of the drug delivery device described herein can be made of the same of different biocompatible, non-biodegradable polymer.

The embodiments illustrated and discussed in this specification are intended only to teach those skilled in the art the best way known to the inventors to make and use the invention. Nothing in this specification should be considered as limiting the scope of the present invention. All drawings presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A drug delivery device, comprising:
    a hollow cylindrical barrel extending between distal and proximal ends, comprising an inner surface and an outer surface, wherein the inner surface comprises helical threads;
    a screw situated within the barrel extending between distal and proximal ends, comprising a hollow cylinder comprising an inner surface and an outer surface, wherein the outer surface comprises helical threads, wherein the helical threads of the outer surface of the screw extend at least a portion of the length of the screw, wherein the helical threads of the outer surface of the screw are engaged with the helical threads on the inner surface of the barrel, wherein the engagement between the threads of the outer surface of the screw and the threads of the inner surface of the barrel is a threaded engagement, whereby the screw rotates as it translates axially along the length of said barrel;
    a plunger extending between distal and proximal ends, wherein the distal end of the plunger engages the proximal end of the screw, wherein axial force applied on the proximal end of the plunger in the distal direction causes the screw to translate distally within the barrel;
    a drug container extending between distal and proximal ends, wherein the proximal end of the drug container is fixed to the screw and the distal end of the drug container is fixed to the barrel and wherein the drug container comprises an outlet port at the distal end; and
    a needle attached to the distal end of the drug container, whereby motion of the plunger in the distal direction causes rotation and translation of said screw, whereby said rotation is imparted to the proximal end of the drug container, whereby said drug container is twisted, whereby the contents of the drug container are expelled through said needle.

2. The drug delivery device of claim 1, further comprising a clamp, wherein the clamp is located within the screw and wherein the clamp engages the proximal end of the drug container.

3. The drug delivery device of claim 1, wherein the drug container comprises hemispherical proximal and distal ends.

4. The drug delivery device of claim 1, wherein the drug container further comprises at least one groove.

5. The drug delivery device of claim 1, wherein the drug container is made of a flexible material.

6. The drug delivery device of claim 1, wherein the drug container further comprises a Frangible Seal at the distal end of the drug container.

7. The drug delivery device of claim 1, wherein the drug container contains a drug.

8. The drug delivery device of claim 7, wherein the drug in the drug container is oxytocin or carbetocin.

9. The drug delivery device of claim 1, wherein the drug delivery device is manufactured using a blow-fill-seal process.

10. The drug delivery device of claim 1, wherein the drug delivery device is manufactured using a form-fill-seal process.

11. The drug delivery device of claim 1, wherein the drug container tapers from the distal end to the proximate end.

* * * * *